United States Patent [19]

Dishler

[11] Patent Number: 5,567,733
[45] Date of Patent: Oct. 22, 1996

[54] IRRITATION RELIEF USING NONSTEROIDAL ANTI-INFLAMMATORY COMPOUNDS

[76] Inventor: Jon G. Dishler, 6295 S. Macon Way, Englewood, Colo. 80111

[21] Appl. No.: 429,833

[22] Filed: Apr. 27, 1995

[51] Int. Cl.$^6$ .................................................. A61K 31/135
[52] U.S. Cl. .................................................. 514/567
[58] Field of Search .................................................. 514/567

[56] References Cited

U.S. PATENT DOCUMENTS

| | | | |
|---|---|---|---|
| 5,234,957 | 8/1993 | Mantelle | 514/772.6 |
| 5,458,879 | 10/1995 | Singh et al. | 424/400 |
| 5,464,609 | 11/1995 | Kelm et al. | 424/54 |

OTHER PUBLICATIONS

Martindale, The Extra Pharmacopoeia, 30th edition, p. 998. 1993.
"Human Transbuccal Absorption of Diclofenac Sodium from a Proto–type Hydrogel Delivery Device", *Pharmaceutical Research*, vol. 10, No. 1 (1993).

*Primary Examiner*—Raymond Henley, III
*Attorney, Agent, or Firm*—Timothy J. Martin; Michael R. Henson

[57] ABSTRACT

A method of relieving irritation to a patient's mucous membrane is provided and comprises contacting the mucous membrane with a non-steroidal anti-inflammatory agent, such as diclofenac sodium, that may be instilled as a spray of drop-wise into the nasopharynx mucosa. The same methodology can also be employed to relieve irritation of a patient's nasopharynx mucosa resulting from anesthesia by endotracheal intubation. A method of administering anesthesia in order to reduce irritation of the tracheal mucosa is also provided and comprises the steps of instilling a quantity of diclofenac sodium solution into the patient's tracheal mucosa, allowing the diclofenac sodium to operate for a selected interval of time, intubating the patient with an anesthesia delivery tube after this interval of time, and delivering a selected anesthesia to the patient.

20 Claims, No Drawings

IRRITATION RELIEF USING NONSTEROIDAL ANTI-INFLAMMATORY COMPOUNDS

FIELD OF THE INVENTION

The present invention broadly concerns methods of relieving irritation of a patient's mucous membrane. More particularly, however, the present invention concerns relief of irritation to the mucous membranes located in nasopharyngeal passageway. Specifically of concern is the relief of irritation which results from the endotracheal intubation of the patient, especially during anesthesia.

BACKGROUND OF THE INVENTION

Irritation of various mucous membranes can result from a variety of factors. On one hand, irritation may result from infections of the mucous membrane by a disease entity, such as occurs with strep throat. On the other hand, irritation of the mucous membranes can be caused directly by physical trauma to the mucous membrane, for example, by surgery or by abrasion from the insertion of a medical instrument. For example, the mucous membranes associated with the nasopharyngeal passage may be traumatized by insertion of a medical instrument such as a nasogastric tube, an anesthesia tube and the like. Types of surgery which can traumatize the nasopharyngeal passageway include tonsillectomies, tracheostomies, vocal cord surgery, etc. Here, irritation may occur to the buccal membrane, the oropharynx, the uvula, the trachea and/or the larynx.

Of particular concern to the present invention, however, is the trauma caused to the various tracheal mucosa resulting from endotracheal intubation which accompanies general anesthesia. Here, an endotracheal tube is inserted into the throat of a patient undergoing general anesthesia, and a cuff is inflated to block the air passageway. The anesthesia is administered through the endotracheal tube. This anesthesia technique can traumatize the tracheal mucosa in several ways. First, the physical rubbing of the endotracheal tube against the tracheal mucosa tends to irritate this mucous membrane. The irritation can be exacerbated by the inflation of the cuff provided on the device. Second, the tracheal mucosa may be damaged by the anesthesia itself or by desiccation from the anesthetic agent. As a result, the patient typically experiences extreme discomfort following anesthesia in the form of a painful sore throat, which condition may persist for several days.

Where a painful irritation of a mucous membrane results from a disease entity, it is not uncommon for a physician to prescribe a steroidal compound to alleviate the symptoms. One such example is the use of cortisone in cases where patient experiences extreme discomfort. The use of steroidal agents, however, are not generally prescribed for other trauma to a mucous membrane. Steroid compounds, of course, work by reducing swelling and have limited topical effect. They have the disadvantages of being slow acting or non-acting where the pain mechanism does not have associated swelling. Also, steroid compounds have the disadvantages of increasing the patient's susceptibility to secondary infections and having limited topical effect so that they are slow-acting. Topical anesthetics are sometimes prescribed, such as xylocaine (viscous 4%), benzocaine and the like. Topical anesthetics can work quickly, but are typically give relief for only a short duration.

Further, while various nonsteroidal anti-inflammatory agents are known, they are not prescribed for conditions of irritation to the mucous membranes, in general, or to the irritation of the tracheal mucosa resulting from intubation, in particular. Non-steroidal anti-inflammatory agents have long been prescribed for systemic use, but, except for a limited use in the eye, have not been used topically. One non-steroidal anti-inflammatory drug, diclofenac sodium, has been topically used as an ophthalmic for dilation of the eye but is known to desensitize the epithelial layer of the eye from pain caused by abrasion or other irritations, especially as may accompany surgery of the eye. Thus, diclofenac sodium is sometimes used topically in the eye for such purposes. Of course, the epithelial layer, however, is not a mucous membrane, such that the use of diclofenac sodium on a mucous membrane is not suggested by this known regimen. Indeed, the cellular structure differences between a mucous membrane and the corneal epithelium are substantial. The corneal epithelium is a stratified squamous epithelium having no secretory cells. A mucous membrane, however, contains a high percentage of secretory cells and is histologically distinct.

It is known that diclofenac sodium, that has a chemical formula of 2-[(2,6-dichlorophenyl) amino]benzeneacetic acid, monosodium salt; $C_{14}H_{10}Cl_2NO_2Na$, will penetrate various membranes, as described in "Human Transbuccal Absorption of Diclofenac Sodium From a Proto-type Hydrogel Delivery Device", Pharmaceutical Research, Vol. 10, No. 1 (1993). In this article, hydrogel disks were loaded with diclofenac sodium in methanol-water. The hydrogel disk was placed on a non-permeable patch and then affixed by dental adhesive to the center of the patient's cheek with a non-permeable patch so that the hydrogel contacted the buccal mucosa for a period of four hours. The purpose of the study was to determine if the diclofenac sodium would penetrate the membrane and enter the blood stream. Accordingly, blood was withdrawn from the volunteer at varying intervals and assayed. In each case, the volunteer for the study was healthy so that the buccal membrane was not previously traumatized, and the study was not directed to examine the effect of the diclofenac sodium on the buccal membrane or to evaluate any relief of irritation arising from the diclofenac sodium.

Accordingly, despite the various drugs available for the relief of irritation to mucous membranes, a need remains for agents which can adequately relieve pain and irritations to the mucous membranes without the disadvantages which accompany steroidal agents and existing topical anesthetics. Moreover, a long felt need has existed for a simple and effective technique of relieving irritation which results from the intubation of patients during anesthesia by relatively benign compounds.

SUMMARY OF THE INVENTION

It is an object of the present invention to provide a new and useful method of treating irritation to a mucous membrane.

Another object of the present invention is to provide a method of relieving irritation to the mucous membrane without the use of steroidal agents.

Still a further object of the present invention is to provide a method of treating irritation to mucous membranes using a non-steroidal anti-inflammatory agent such as diclofenac sodium.

Yet another object of the present invention is to provide a method of relieving tracheal irritation of the tracheal mucosa resulting from anesthesia by tracheal intubation.

Still a further object of the present invention is to provide a method for treating tracheal irritation which can be easily self-administered by the patient in a safe and effective manner.

A further object of the present invention is to provide a method of administering anesthesia in a manner to reduce post-anesthesia pain to the patient.

According to the present invention, then, a method of relieving irritation to a mucous membrane of a patient broadly comprises the step of contacting the mucous membrane with a non-steroidal anti-inflammatory agent. Preferably, this non-steroidal anti-inflammatory agent is diclofenac sodium.

In particular, however, the method of the present invention is directed to relieving tracheal irritation of the tracheal mucosa of a patient which results from anesthesia by endotracheal intubation. Here, the method broadly includes the step of contacting the tracheal mucosa of the patient with an effective amount of a non-steroidal anti-inflammatory agent, such as diclofenac sodium. More specifically, however, the method according to the present invention instills the diclofenac sodium as a spray or drop-wise onto the tracheal mucosa.

The method of the present invention may further be directed to a method of administering anesthesia to a patient in a manner to reduce the irritation of the nasopharynx mucosa comprising the steps of instilling a quantity of diclofenac sodium solution onto the nasopharynx mucosa prior to intubation of the patient. Next, a selected interval of time is allowed to lapse to allow the diclofenac sodium to penetrate the nasopharynx mucosa. Next, the patient is intubated with an anesthesia delivery tube, and the selected anesthesia is delivered to the patient.

These and other objects of the present invention will become more readily appreciated and understood from a consideration of the following detailed description of the exemplary embodiment.

DETAILED DESCRIPTION OF THE EXEMPLARY EMBODIMENTS

The present invention is directed generally to the topical use of non-steroidal anti-inflammatory agents in the treatment of irritation to mucous membranes. Specifically, however, the present invention is directed to a method of treating irritation to the nasopharynx mucosa which has resulted from the administration of a general anesthesia to a patient, such as occurs during tracheal intubation with an anesthesia delivery device. Thus, the present invention also concerns methods of administering general anesthesia to a patient. Specifically, this methodology incorporates the installation of diclofenac sodium onto the tracheal mucosa.

STUDY A

An initial indication that diclofenac sodium had the capability of reducing and even eliminating irritation to the tracheal membrane was conducted on a single patient, K.P., who had undergone general anesthesia by endotracheal intubation for nasal surgery. Unfortunately, during the use of the endotracheal tube, the uvula of the patient was crushed to a degree that the mucous membrane covering the uvula necrosed. Severe inflammation and pain resulted. The patient was treated by her plastic surgeon with analgesics for this pain, but she experienced little or no relief. As a test, it was suggested that diclofenac sodium could be applied topically to the uvula in a drop-wise manner which might relieve pain. A composition containing 0.1% (1 mg/mL) diclofenac sodium as an active ingredient and sold under the trademark Voltaren® (available from CIBAVision Ophthalmics of Atlanta, Ga.) was employed for this initial test. The inactive ingredients in this compound include boric acid, edetate disodium (1 mg/mL), polyoxyl 35 castor oil, purified water, sorbic acid (2 mg/mL) and tromethamine. Two to three drops of this compound was topically applied so that it contacted the uvula. This individual reported almost instantly (within three (3) minutes), dramatic relief from pain, and this relief lasted about four (4) hours. Accordingly, the individual instilled this solution, drop-wise, onto the uvula with the administration of approximately two to three drops every four (4) hours, and this regimen proved successful.

Accordingly, more expanded studies was designed for a larger population of patients who were receiving general anesthesia by tracheal intubation for various cosmetic surgery. Two such studies were performed. The results are as follows:

STUDY B

In this test, approximately two to three drops of the diclofenac sodium solution (Voltaren®) was mixed with approximately 2 cc of a water soluble lubricating ointment, and this mixture was applied to a distal portion of the endotracheal tube which contacts the tracheal mucosa during general anesthesia. The patient was then intubated with endotracheal tube so that the ointment containing the diclofenac sodium was placed in contact with the trachea. This technique was used with a total of seven patients, and the patients were then queried following general anesthesia to determine whether any discomfort resulted from the intubation. The results are reported in the following Table I:

TABLE I

| Patient | Surgery Type | Post-Intubation Discomfort |
| --- | --- | --- |
| C. C. | Liposuction | Yes |
| N. R. | Cepsulection | Yes |
| R. B. | Blepharoplasty | Some |
| K. J. | Septo Rhino | No |
| A. A. | Face Lift | Yes |
| J. S. | Stomach Tuck | Some |
| M. R. | Body Lift | Some |

Accordingly, it was learned from this initial study of the seven patients that substantial discomfort still resulted in three of the patients although four patients received some relief from discomfort. One patient, K. J., reported no discomfort. Accordingly, it appeared that some relief to tracheal irritation occurred by the incorporation of the diclofenac sodium in to the lubricating ointment, it was thought that the ointment sufficiently diluted the amount of diclofenac sodium which reached the mucous membrane. Thus, it is proposed that a larger quantity of diclofenac sodium be used if placed in the lubricating ointment.

STUDY C

Accordingly, a second test was devised wherein the tracheal mucosa was contacted directly with the Voltaren® solution without incorporating the solution into the lubricating ointment. Here, approximately 0.25 cc of Voltaren was instilled directly as a spray onto the vocal cords and the trachea of the patient prior to intubation for general anesthesia. A blunted and curved 22 gauge needle and syringe was used as the delivery vehicle and contact of the mucous membrane by the spray was visually confirmed. After spraying the tracheal mucosa with the diclofenac solution, an interval of approximately one to five minutes was allowed to lapse before the patient was intubated. A group of fifteen patients were studied utilizing this technique, and the results were dramatic. These results are reported in the following Table II:

TABLE II

| Patient | Surgery Type | Post-Intubation Discomfort |
|---|---|---|
| K. O. | Breast Augmentation and Rhinoplasty | No |
| M. R. | Excision Multiple Cysts | No |
| R. W. | Reduction Fracture (Nose) | No |
| K. T. | Face Lift | No |
| P. W. | Liposuction | No |
| K. R. | Septo Rhinoplasty | No |
| S. L. | Face Lift | No |
| K. K. | Excision Mass Chest | No |
| P. P. | Mastopexy | No |
| C. P. | Capsulectomy | No |
| E. E. | Mammoplasty | No |
| M. L. | Face Lift | No |
| C. H. | Stomach Tuck | No |
| H. T. | Rhinoplasty | Minimal |
| C. P. | Blepharoplasty | No |

As can be seen in Table II, all fifteen patients reported relief from irritation resulting from the intubation for the general anesthetic. Only one patient out of the fifteen reported any discomfort, and this discomfort was rated by the patient as minimal.

Diclofenac sodium, as noted above, falls in the general class of non-steroidal anti-inflammatory compounds. It's method of pain suppression appears to be the on-site blockage of nerve pulses. The relief that occurred to the patients was rapid enough to rule out an anti-inflammatory relief mechanism as providing the pain suppression, and the pain blockage would not be a central nervous system blockage due to the topical application.

From the results of these studies, it would appear that other non-steroidal, anti-inflammatory compounds such as flurbiprofen, ketorolac and suprofen, among others, might hold promise in suppressing pain arising from irritation to the various mucous membranes. Indeed, there is the potential to use such mild non-steroidal anti-inflammatories to give relief in many existing situations from oral surgery to urogenital surgery, as well as from pain of diseases that result in inflammation or irritation of a mucous membrane.

Accordingly, the present invention has been described with some degree of particularity directed to the exemplary embodiment of the present invention. It should be appreciated, though, that the present invention is defined by the following claims construed in light of the prior art so that modifications or changes may be made to the exemplary embodiment of the present invention without departing from the inventive concepts contained herein.

I claim:

1. A method of relieving irritation to a mucous membrane of a patient comprising contacting the mucous membrane with a composition having an active ingredient consisting essentially of a non-steroidal anti-inflammatory agent.

2. A method of relieving irritation according to claim 1 wherein said non-steroidal anti-inflammatory agent is diclofenac sodium.

3. A method of relieving irritation according to claim 1 wherein said mucous membrane is a nasopharynx mucosa of said patient.

4. A method of relieving irritation of the nasopharynx mucosa of a patient resulting from anesthesia by endotracheal intubation comprising the step of contacting the nasopharynx mucosa of said patient with composition consisting essentially of a non-steroidal anti-inflammatory agent as an active ingredient.

5. A method of relieving irritation according to claim 4 wherein said non-steroidal anti-inflammatory agent is diclofenac sodium.

6. A method of relieving irritation according to claim 5 wherein said diclofenac sodium is instilled as a spray onto the nasopharynx mucosa.

7. A method of relieving irritation according to claim 5 wherein said diclofenac sodium is instilled drop-wise onto the nasopharynx mucosa.

8. A method of relieving irritation according to claim 5 wherein the tracheal mucosa is contacted with between 0.1 ml and 0.5 ml of a composition containing about 0.1% (1 mg/mL) diclofenac sodium.

9. A method of administering anesthesia to a patient in a manner to reduce irritation of the tracheal mucosa comprising the steps of:

(a) instilling a quantity of diclofenac sodium solution onto the tracheal mucosa;

(b) allowing said diclofenac sodium to operate for a selected interval of time;

(c) intubating the patient with an anesthesia delivery tube after the selected interval; and (d) delivering a selected anesthesia to the patient.

10. A method of administering anesthesia according to claim 9 wherein said diclofenac sodium solution is in a water-based carrier solvent and the step of instillation is accomplished by spraying or dripping said solution directly on the tracheal mucosa.

11. A method of relieving irritation to a mucous membrane of a patient comprising the step of instilling onto the mucous membrane a composition containing diclofenac sodium as a majority active ingredient in a carrier solution.

12. A method of relieving irritation according to claim 11 wherein said mucous membrane is a nasopharynx mucosa of said patient.

13. The method of claim 11 wherein said non-steroidal anti-inflammatory agent is instilled as a spray onto the mucosa.

14. The method of claim 11 wherein the non-steroidal anti-inflammatory agent is instilled drop-wise onto the mucosa.

15. A method of relieving irritation to a mucous membrane of a patient comprising the step of instilling onto the mucous membrane a quantity of a non-steroidal anti-inflammatory agent as an active ingredient in a carrier compound wherein said quantity of the non-steroidal anti-inflammatory agent is sufficient to induce an anesthetic blockage of nerve pulses locally in the mucous membrane.

16. A method of relieving irritation according to claim 15 wherein said non-steroidal anti-inflammatory agent is diclofenac sodium.

17. A method of relieving irritation according to claim 16 wherein said carrier compound includes water as a solvent carrier, boric acid, edetate disodium, castor oil and sorbic acid.

18. A method of relieving irritation according to claim 15 wherein said mucous membrane is a nasopharynx mucosa of said patient.

19. The method of claim 15 wherein said non-steroidal anti-inflammatory agent is instilled as a spray onto the mucosa.

20. The method of claim 15 wherein the non-steroidal anti-inflammatory agent is instilled drop-wise onto the mucosa.

* * * * *

US005567733B1

REEXAMINATION CERTIFICATE (3847th)

United States Patent [19]
Dishler

[11] B1 5,567,733
[45] Certificate Issued Aug. 24, 1999

[54] IRRITATION RELIEF USING NONSTEROIDAL ANTI-INFLAMMATORY COMPOUNDS

[76] Inventor: Jon G. Dishler, 6295 S. Macon Way, Englewood, Colo. 80111

Reexamination Request:
No. 90/004,776, Oct. 10, 1997

Reexamination Certificate for:
Patent No.: 5,567,733
Issued: Oct. 22, 1996
Appl. No.: 08/429,833
Filed: Apr. 27, 1995

[51] Int. Cl.$^6$ .................................................. A61K 31/135
[52] U.S. Cl. ............................................................. 514/567
[58] Field of Search ............................................. 514/567

[56] References Cited

U.S. PATENT DOCUMENTS

| 4,329,366 | 5/1982 | Nashed et al. . |
| 4,765,983 | 8/1988 | Takayanagi et al. . |
| 4,855,142 | 8/1989 | Fankhauser et al. . |
| 5,192,802 | 3/1993 | Rencher . |
| 5,208,035 | 5/1993 | Okuyama et al. . |
| 5,369,131 | 11/1994 | Poli et al. . |

FOREIGN PATENT DOCUMENTS

| 80-163696 | 11/1955 | Japan . |
| 89-111650 | 5/1964 | Japan . |

*Primary Examiner*—Raymond J. Henley, III

[57] ABSTRACT

A method of relieving irritation to a patient's mucous membrane is provided and comprises contacting the mucous membrane with a non-steroidal anti-inflammatory agent, such as diclofenac sodium, that may be instilled as a spray of drop-wise into the nasopharynx mucosa. The same methodology can also be employed to relieve irritation of a patient's nasopharynx mucosa resulting from anesthesia by endotracheal intubation. A method of administering anesthesia in order to reduce irritation of the tracheal mucosa is also provided and comprises the steps of instilling a quantity of diclofenac sodium solution into the patient's tracheal mucosa, allowing the diclofenac sodium to operate for a selected interval of time, intubating the patient with an anesthesia delivery tube after this interval of time, and delivering a selected anesthesia to the patient.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 9–14 is confirmed.

Claims 2, 5 and 16 are cancelled.

Claims 1, 4, 6–8, 15 and 17 are determined to be patentable as amended.

Claims 3, 18, 19 and 20, dependent on an amended claim, are determined to be patentable.

1. A method of relieving irritation to a mucous membrane of a patient comprising contacting the mucous membrane with a *quantity of a flowable fluid* composition having an active ingredient consisting essentially of [a non-steroidal anti-inflammatory agent] *diclofenac sodium*.

4. A method of relieving irritation of the nasopharynx mucosa of a patient resulting from anesthesia by endotracheal intubation comprising the step of contacting the nasopharynx mucosa of said patient with composition consisting essentially of [a non-steroidal anti-inflammatory agent] *diclofenac sodium*.

6. A method of relieving irritation according to claim [5] *4* wherein said diclofenac sodium is instilled as a spray onto the nasopharynx mucosa.

7. A method of relieving irritation according to claim [5] *4* wherein said diclofenac sodium is instilled drop-wise onto the nasopharynx mucosa.

8. A method of relieving irritation according to claim [5] *4* wherein the tracheal mucosa is contacted with between 0.1 ml and 0.5 ml of a composition containing about 0.1% (1 mg/mL) diclofenac sodium.

15. A method of relieving irritation to a mucous membrane of a patient comprising the step of instilling onto the mucous membrane a quantity of [a non-steroidal anti-inflammatory agent] *diclofenac sodium* as an active ingredient in a carrier compound wherein said quantity of [the non-steroidal anti-inflammatory] *diclofenac sodium* is sufficient to induce an anesthetic blockage of nerve pulses locally in the mucous membrane.

17. A method of relieving irritation according to claim [16] *15* wherein said carrier compound includes water as a solvent carrier, boric acid, edetate disodium, castor oil and sorbic acid.

* * * * *